United States Patent [19]

Reider et al.

[11] Patent Number: 4,859,771

[45] Date of Patent: Aug. 22, 1989

[54] PROCESS FOR RESOLUTION AND RACEMIZATION OF AMINES WITH ACIDIC α-HYDROGENS

[75] Inventors: Paul J. Reider; Edward J. J. Grabowski, both of Westfield, N.J.

[73] Assignee: Merck & Co., Inc., Rahway, N.J.

[21] Appl. No.: 300,737

[22] Filed: Jan. 19, 1989

Related U.S. Application Data

[63] Continuation of Ser. No. 178,872, Mar. 30, 1988, abandoned, which is a continuation of Ser. No. 885,047, Jul. 14, 1986, abandoned.

[51] Int. Cl.$^4$ ............... C07B 55/00; C07D 243/00
[52] U.S. Cl. ............... 540/509; 540/570; 564/302; 564/303; 564/304
[58] Field of Search ............... 540/509, 570

[56] References Cited

U.S. PATENT DOCUMENTS

| | | | |
|---|---|---|---|
| 1,954,389 | 4/1934 | Legerlotz | 564/302 X |
| 2,608,583 | 8/1952 | Aschner | 564/302 |
| 3,555,093 | 1/1971 | L'Italien | 564/304 X |
| 3,819,689 | 6/1974 | Thompson et al. | 564/304 X |
| 3,852,274 | 12/1974 | Kajfez et al. | 540/509 X |
| 3,899,527 | 8/1975 | McCaulty | 564/328 X |
| 4,628,084 | 12/1986 | Bock et al. | 540/509 |

FOREIGN PATENT DOCUMENTS 0253571  1/1988  European Pat. Off. ............ 540/409

OTHER PUBLICATIONS

Clark et al., "Jour. Chem. Soc., Perkin I", pp. 475–481, (1976).
"The Merck Index", 10th Ed., p. 239, Section No. 1712, (1983).
Stinson, S. C., Chem. Eng. News, Issue of Oct. 19, 1987, pp. 30–33.

Primary Examiner—Donald G. Daus
Attorney, Agent, or Firm—Roy D. Meredith; Hesna J. Pfeiffer

[57] ABSTRACT

An economical, one-pot process for resolution-racemization of primary amines with α-hydrogens via selective crystallization of diastereomeric chiral sulfonic acid salts and the subsequent in situ racemization of the other enantiomer by the catalytic addition of aromatic aldehydes, and a key process intermediate thereof.

4 Claims, No Drawings

PROCESS FOR RESOLUTION AND RACEMIZATION OF AMINES WITH ACIDIC α-HYDROGENS

This is continuation of application Ser. No. 178,872, filed Mar. 30, 1988, now abandoned which is a continuation of Ser. No. 885,047, July 19, 1986, now abandoned.

The instant invention is directed to a one-pot process for the resolution-racemization of primary amines with α-hydrogens via selective crystallization of diastereomeric chiral sulfonic acid salts and the subsequent in situ racemization of the other enantiomer by the catalytic addition of aromatic aldehydes, which permits the stereo-specific synthesis of the desired isomer.

BACKGROUND OF THE INVENTION

Processes for resolution-racemization of pheny glycine are known (Clark et al, *J. C. S. Perkin* I, 475–481, 1976). However, the known processes require stoichiometric amounts of both a weak, chiral acid and an aromatic aldehyde, which severely limits the processes to applications involving amines considered capable of forming tartrate salts.

It was therefore an object of this invention to develop an economical, one-pot process for the resolution-racemization of weakly-to-moderately basic organic amines containing α-hydrogens employing only a catalytic amount an aldehyde. It was a further object of this invention to develop an efficient process for the preparation and isolation of the optically-pure desired isomer of a chiral sulfonic acid salt.

DESCRIPTION OF THE INVENTION

The present invention is directed to a one-pot, high yield process for the resolution-racemization of primary amines with acidic α-hydrogen the pKa's of which are less than or equal to 15, which comprises adding about 0.86–0.94 mole equivalents of a chiral sulfonic acid in an appropriate organic solvent and about 1 to 5 mole equivalents of water to a solution of a racemic mixture of a primary amine with an to create a resolution mixture; seeding the resolution mixture with a crystalline diastereomeric salt derived from the primary amine and the chiral sulfonic acid; adding a catalytic amount of an aromatic aldehyde to the resolution mixture; and filtering the resolution mixture to isolate the optically-pure diastereomeric salt of the primary amine with an α-hydrogen.

Examples of chiral sulfonic acids useful in this invention are camphorsulfonic acid, specifically (1S)-(+)-10-camphorsulfonic acid, and bromocamphorsulfonic acid, for which appropriate organic solvents (solvents in which the chiral sulfonic acid is soluble) would be an organic ester, such as methyl acetate, ethyl acetate, isopropyl acetate and butyl acetate; an organic ether, such as diethyl ether, methyl-t-butyl ether, tetrahydrofuran, dioxane and dimethoxyethane; acetonitrile; or mixtures thereof. Useful aromatic aldehydes include benzaldehyde, salicylaldehyde, 3,5-dichlorosalicylaldehyde and p-NO2benzaldehyde, the catalytic amount of which for effecting racemization of the unwanted isomer of the selected primary amine after crystallization of the desired isomer has occurred in the resolution mixture, is generally about 3 to 5 mole %, based on the calculated amount of mixture present.

The process is useful for primary amines with acidic α-hydrogens, including, for example, 3-amino-diazepin-2-ones, such as 3(R,S)-amino-1,3-dihydro-1-methyl-5-phenyl-2H-1,4-benzodiazepin-2-one, for which a key process intermediate in resolution-racemization process of the present invention is 3(S)-amino-1,3-dihydro-1-methyl-5-phenyl-2H-1,4-benzodiazepin-2-one, camphorsulfonic acid salt.

Specifically, the schematic of the process according to this invention may be represented by:

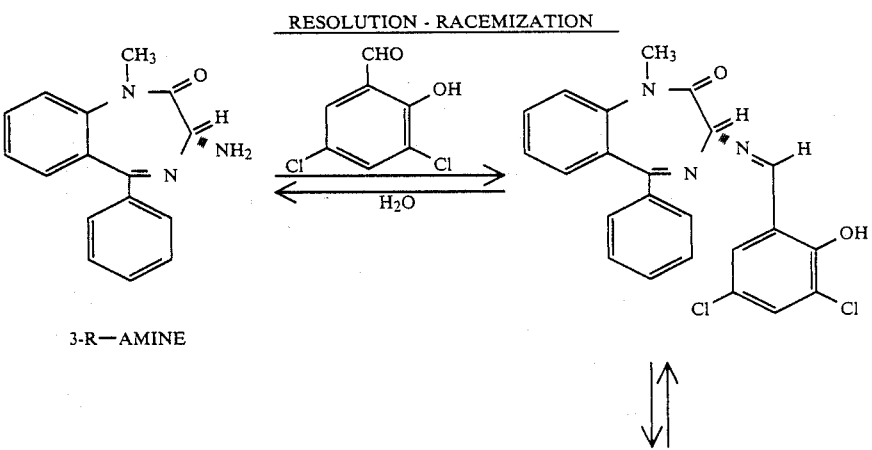

-continued
RESOLUTION - RACEMIZATION

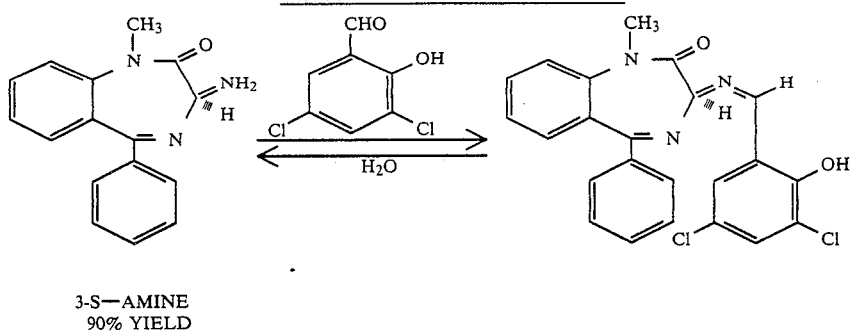

3-S—AMINE
90% YIELD

The racemic amine is resolved by selectively crystallizing the 3-S-amine as its (1S)-(+)-10-camphorsulfonic acid (CSA) salt. Treatment of a solution of (±) amine with 0.5 equivalent CSA and seeding the effects with crystals isolated from an oily mixture of the 3-aminodiazepin-2-one and CSA in ethyl acetate-ether, in, for example, ethyl acetate, ispropyl acetate, or acetonitrile, results in the 3-S-amine CSA with greater than 99.5% enantiomeric pruity. Isolated yields are generally 40–42%, with the mother liquors containing an approximately 90:10 ratio of the 3R:3S amine, and the isolated 3-S-amine CSA salt appearing to be a hemi-hydrate. The addition of small amounts of water to the resolution mixture (KF range=0.5–3.0 mg/ml) optimizes the crystallization.

The racemization of the unwanted 3-R-isomer is then achieved by addition of a catalytic amount (3–5%) of an aromatic aldehyde, and an equilibrium concentration.

of imine is established. The acidity of the alpha proton is thus increased, allowing the chiral center to racemize at ambient temperature and basicity.

In the presence of 0.86–0.94 moles of CSA, the crystalline 3-S-amine CSA salt is essentially removed from the equilibrium system by virture of its insolubility, resulting in the 3-R-mine being continuously shunted through the imines to the desired 3-S-amine.

This combined resolution-racemization is easily run. The racemic amine is dissolved in isopropyl acetate and treated with 86 to 94 mole % CSA in $CH_3CN$ (with appropriate seeds of the desired end-product) to give generally greater than 40% crystallization of the 3-S-amine CSA (by assay of the supernatant). The introduction of generally 3 to 5 mole % of 3,5-dichlorosalicylaldehyde to the reaction slurry then causes racemization with a t½ of about six hours at 24 C.

After a total of about 36 hours, the product is isolated by filtration in approximately 83% yield based on amine or approximately 97% yield based on the limiting reagent, CSA. The rate of racemization does increase with temperature, but there is some accompanying decomposition, and if greater than 90 mole % CSA is charged, the rate of racemization slows, with the use of greater than or equal to 100 mole % CSA virtually preventing the racemization. In the event of a CSA overcharge, the addition of free amine will reinitiate the racemization.

The following example is intended to further illustrate the invention, without limiting it.

Example 1
Preparation of 3(S)-amino-1,3-dihydro-1-methyl-5-phenyl-2H-1, 4-benzodiazepin-2-one, camphorsulfonate salt

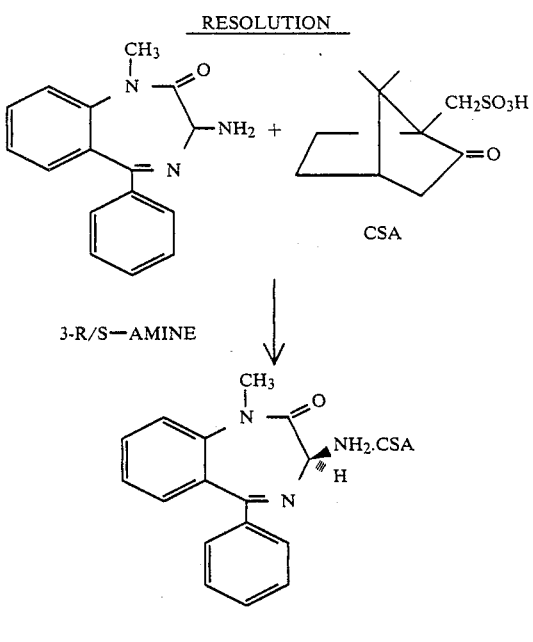

3-S—AMINE CSA SALT

A solution of 1.367 moles of the racemic amine prepared according to Examples 183 and 184 from EPO published application 167 919 in isopropyl acetate (6000 ml) was assayed (HPLC, titration) and 86 mole % of (1S)-(+)-l0-camphorsulfonic acid (CSA) (273 g. 1.17 moles) in acetonitrile (1600 %1), (i.e.: 0.75 M solution) was added, while maintaining the temperature ≦20? C, with the mixture being seeded with 1.0 g of 3-S amine CSA when ca. 50% of the CSA had been charged. The white suspension was allowed to warm to 20–5° C. and was aged for 4 hours, at which time the supernatant was assayed.

When 35–42% of the amine (70–84% of the 3-S-amine) was our of solution as the CSA salt (by assay of the supernatant), the mixture was treated with 7.8 g (0.04 mole, 3 mole %) of 3,5-dichlorosalicylaldehyde and the slurry was aged, with stirring, at 20–30 °C. for 36 hours. Upon completion of the resolu slurry was filtered and the cake washed with isopropyl acetate (3000 ml — as a 2000 ml slurry wash followed by a 1000 ml displacement wash). After a hexane wash (6000 ml) the product was vacuum dried (25° C.). Yield 565 g (83%).

HPLC (wt %) ≧98% as amine (corrected), (chiral) ≧99.8% 3-S isomer.

What is claimed is:

1. A process for the resolution-racemization of a 3 amino diazepin 2 one which comprises:
   (a) adding about 0.86 - 0.94 mole equivalent of a chiral sulfonic acid in an appropriate organic solvent and from about one to about 5 mole equivalent of water to a solution of a racemic mixture of a 3 amino diazepin-2-one to create a resolution mixture;
   (b) seeding the resolution mixture with a crystalline diastereomeric salt derived, from said 3 amino diazepin 2-one and said chiral sulfonic acid;
   (c) adding a catalytic amount of an aromatic aldehyde to the resolution mixture; and
   (d) filtering the resolution mixture to isolate the optically-pure diastereomeric salt of said 3-amino diazepin 2 one.

2. A process according to claim 1, wherein the chiral sulfonic acid is a camphorsulfonic acid or a bromocamphorsulfonic acid; the appropriate organic solvent is an organic ester, an organic ether, acetonitrile or a mixture thereof; the aromatic aldehyde is salicyladehyde, 3,5-dichlorosalicylaldehyde, benzaldehyde or p-NO$_2$benzaldehyde and the catalytic amount of said aromatic aldehyde is from about three to about five mole percent.

3. A process according to claim 2, wherein said 3-amino diazepin-2-one is 3(R,S,)-amino 1,3 dihydro-1-methyl -5-phenyl-2H 1,4 benzo diazepin 2-one; the chiral sulfonic acid is (1S)-(+)-10 camphorsulfonic acid; the appropriate organic solvent is a mixture of isopropyl acetate and acetonitrile; and the aromatic aldehyde is 3,5-dichlorosalicyclaldehyde.

4. 3(S)-amino-1,3-dihydro-1-methyl-5-phenyl-2H-1, 4-benzodiazepin-2-one, (1S)-(+)-10-camphorsulfonate salt.

* * * * *